United States Patent [19]

Colas

[11] 3,973,003
[45] Aug. 3, 1976

[54] PROCESS FOR THE PRESERVATION OF RAM SEMEN BY FREEZING

[75] Inventor: Guy Colas, Tours, France

[73] Assignee: Institut National de la Recherche Agronomique, Paris, France

[22] Filed: Dec. 16, 1974

[21] Appl. No.: 533,382

[30] Foreign Application Priority Data
Dec. 18, 1973 France ............................. 73.45351

[52] U.S. Cl. .................................. 424/105; 195/1.8
[51] Int. Cl.$^2$ ..................... A61K 35/52; C12K 9/00
[58] Field of Search ....................... 195/1.8; 424/105

[56] References Cited
UNITED STATES PATENTS 3,185,623  5/1965  Smith et al. ........................... 195/1.8
3,431,172  3/1969  Rajamannan ....................... 195/1.8

Primary Examiner—Sam Rosen
Attorney, Agent, or Firm—Burgess, Dinklage & Sprung

[57] ABSTRACT

The process according to the invention consists in that the freshly collected ram semen is first diluted at between 25° and 32°C and notably at 30°C, in a diluent without glycerol containing lactose and egg yolk, and in then diluting, at between 3° and 5°C and notably at 4°C, the mixture previously obtained in a diluent containing glycerol, said diluent essentially comprising powdered milk and sodium citrate, in conditioning in straws the so diluted semen and in freezing it in liquid nitrogen at about −75°C. The invention also relates to the diluent used in the above process.

The process is useful for preserving ram semen by freezing for subsequent artificial insemination of ewes.

15 Claims, No Drawings

PROCESS FOR THE PRESERVATION OF RAM SEMEN BY FREEZING

The present invention relates to a process for the preservation of ram semen by freezing. Another object of the present invention is the means for carrying out said process and the products obtained.

In the breeding of domestic animals, and notably ovines, artificial insemination is used with ever increasing frequency, and processes for preserving ram semen in the liquid or frozen state have already been proposed.

The already known process for preservation by freezing consist, generally speaking, in diluting the freshly collected semen in a suitable diluent and in freezing the thus obtained solution, by the straw, ampulla or pellet freezing techniques. The diluents used in said processes are diluents consisting of milk or egg yolk and containing glycerol. The results obtained (percentages of lambing) are very variable, according to the conditions under which the process is carried out (nature of the diluent, dilution temperature, glycerol level, freezing technique) and the technique of insemination.

J. Aamdal and Kandersen ["Freezing of ram semen in straws" (VIth international congress on animal reproduction by artificial insemination, Paris, 1968 volume II, p.977–980)] use a lactose-containing diluent of the type proposed by NAGASE and GRAHAM [Diluted semen: Comparison of different extenders and processes on fertility of bovin spermatozoa, Vth international congress on animal reproduction by artificial insemination, TRENTO, IV, 1964 p.387–391], containing 11% lactose, 20% egg yolk and 4.7% glycerol. After dilution, the semen is stored at 4°–5°C and conditioned in straws and then frozen in liquid nitrogen. Artificial insemination of ewes with the so preserved ram semen resulted in 62% pregnancies after two inseminations in the same heat.

A. F. FRASER ["Progress in the artificial insemination of sheep with frozen semen" (VIth international congress on animal reproduction by artificial insemination, Paris, 1968, volume II, p.1033–1035)] also uses a diluent of the NAGASE and GRAHAM type containing 25% egg yolk, 71.5% of a 11% lactose solution and 3.5% glycerol. Freezing is carried out by the pelleting method; the percentage of lambing was only 31% after one insemination.

W. KARETA et al ["Fertility of frozen semen diluted in citrate added bull seminal plasma or not" (VII th International congress of animal reproduction by artificial insemination, Munich (1972) p.1479 to 1484)] used, for the freezing of ram semen by the technique known as in ampulla, either a mixture of egg yolk, fructose, glycerol and sodium citrate, or the same mixture added bull seminal plasma; the results obtained (percentage of lambing) were 50% with the first diluent and 61% with the second.

The diluents proposed by MARTIN ["Milk and synthetic diluents for ram semen" (VIth international congress on animal reproduction by artificial insemination, Paris 1968, volume II, pages 1619–1622)] contain milk, fructose, another sugar selected from glucose, arabinose, lactose, etc., sodium chloride, a phosphate pH buffer and glycerol. The percentage of mobility of the spermatozoa in the thawed semen varied according to the second sugar used.

LUNCA ["Some aspects of the freezing of ram semen" (VIth international congress of animal reproduction by artificial insemination, Paris, 1968 volume II, pages 1615–1618)] described, among other things, a diluent containing fresh sterilized and skimmed cowmilk, egg yolk and glycerol. 35 to 50% motility of spermatozoa was observed after thawing, and motility was 35 to 45% after 5 days of freezing.

CARBONERO BRAVO compares various glycerol-containing diluents in the article "Das Tiefgefrieren von Schafbocksamen" [VIIth international congress on animal reproduction by artificial insemination, Munich (1972) p.1496–1499)]. One of said diluents contains sodium citrate, powdered milk and glycerol; the motility of spermatozoa was 20 to 40% after freezing and thawing of semen in the above diluent. The results obtained with milk-containing diluents were not better than those obtained with lactose containing diluents.

COLAS and BRICE [Ann. Zootech 1970, 19 (3) 353–357] have described a process for the preservation of ram semen consisting in first prediluting at 30°C the semen collected from rams in a diluent containing no glycerol, of the type proposed by NAGASE and GRAHAM, and in then diluting at 4°C the prediluted semen in the same diluent containing 10% glycerol. The temperature is lowered from 30° to 4°C in 2 hours. Glycerolization lasts for about 2 hours, and the so diluted semen is frozen in liquid nitrogen. The average percentage of lambing is about 60%.

It is an object of the present invention to provide a process which allows, after thawing, to obtain semen providing constant, high, lambing, rates.

The process for preserving ram semen by freezing according to the invention comprises the following steps of diluting freshly collected ram semen first at a temperature from about 25° to 32°C, and notably at about 30°C in a diluent without glycerol and containing lactose and egg yolk; (2) then diluting the mixture so obtained at a temperature from about 3° to 5°C, and notably at about 4°C, in a diluent with glycerol, said diluent essentially comprising powdered milk and sodium citrate; (3) conditioning in straws the so diluted semen in known manner and freezing it in liquid nitrogen at about −75°C.

In practice, the temperature is lowered in about two hours between the two dilution steps. However the above durations may somewhat vary. Thus, the lapse of time between the two dilution steps can be as long as 3 hours, although it is not generally speaking advisable to increase it for much longer than this period. To obtain good preservation of semen, it is preferable not to cool it too quickly after the first dilution, so that times shorter than 2 hours should generally be avoided. In practice, the second dilution is preferably carried out in two steps at 20 minute intervals, and the contact of the diluted semen with the second diluent lasts for 2 hours to 2 and one half hours. However, it is also possible to perform the second dilution by adding the glycerolated solution to the prediluted semen in one step. Similarly, the contact time with the second diluent can very well last for less than 2 hours and, in this case, the obtained results vary with the final rate of glycerol. For reasons of economy, it is useless to prolong the contact time for longer than 2.5 to 3 hours.

The diluent without glycerol used in the first dilution of the process of the invention hereinafter designated as "diluent 101" is a diluent containing egg yolk and lactose. According to the invention, the diluent 101 contains lactose and preferably up to 20% (volume per volume) of egg yolk. According to the process of the invention, a diluent 101 comprising 80% of a 10.3% lactose solution (by weight per volume) and 20% egg yolk (in volume per volume) is advantageously used. According to the invention, the diluent 101 should be renewed each day and used at a temperature of about 30°C.

The second diluent used in the process of the invention and hereinafter designated as "diluent 102" is a concentrated powdered milk solution containing glycerol, the pH of which has been adjusted to a value of between 6 and 7, and advantageously of 6.60–6.65 by means of a concentrated sodium citrate solution. Said diluent is advantageously prepared from a diluent comprising powdered milk generally used for the preservation of ovine semen in the liquid state and designated hereinafter as "diluent L". A process for obtaining "diluent L" is described by G. COLAS et al. ["Results obtained during the study of some important factors of ovine artificial insemination" (Ann. Zootech, 1968, 17(1), 47, 57)]. Said diluent is an aqueous solution containing about 10.3% powdered milk (weight per volume); the powdered milk known under the trade name "REGILAIT" is used for example as the powdered milk. For the purpose of the present invention, said diluent L should, to be suited for use as the second diluent, be enriched with powdered milk.

According to a preferred embodiment of the process of this invention, the diluent 102 is prepared from diluent L containing 10.3% powdered milk by adding to 100 ml of said diluent L at least 4g of powdered milk known by the trade name "REGILAIT", the pH of the mixture so obtained is then adjusted to 6.60–6.65 by means of a concentrated sodium citrate solution, and bi-distilled glycerol is then added in an amount such that the final glycerol concentration of the diluted semen is at most 4% (volume/volume) The trials in vitro have shown that glycerol concentrations of approximately 2% gave slightly less satisfactory results, and that a concentration of about 7% gave markedly worse results than the recommended concentrations, which are approximately 4%. The diluent 102 according to the invention should be used at 4°C, and preferably prepared each day. According to a preferred embodiment of the process of the invention, the diluent 102 contains 10% by volume of glycerol; the volume of the diluent 102, added at 4°C, called hereinafter volume $V_4$, to be used, is determined so that the final volume $V_T$ of diluted semen contains 4% glycerol; volumes $V_4$ and $V_T$ are thus connected, in this particular case, by the relation $V_4$ = two-fifths $V_T$. Volume $V_T$ is a function of the volume Vo of the pure semen and concentration Co (concentration of spermatozoa in pure semen) and Cf (final concentration); this gives $V_T$ = Co/Cf Vo. The volume of the diluent 101 added at about 30°C, or volume $V_{30}$, is such that the relation $V_{30}$ = $V_T - (V_o + V_4)$ is obtained.

It will be easy for one skilled in the art to determine volumes $V_T$ and $V_4$ to be used according to the initial concentration of glycerol in the volume $V_4$, to the volume Vo, the concentration Co and concentration Cf desired. According to the invention, it was determined that a concentration of 900 × $10^6$ spz/ml (spermatozoa per ml) was a particularly advantageous final concentration of spermatozoa in the diluted semen. Trials have shown that concentrations higher than 900 × $10^6$ spz/ml, for example 1,200 × $10^6$ and 1,500 × $10^6$ spz/ml gave less advantageous survival rates. On the other hand, weaker dilutions than 900 × $10^6$ spz/ml, for example 600 × $10^6$ spz/ml would be desirable, however the volume of the dose of semen to be injected is a limiting factor, as this should not be too large for the ewe. Concentrations weaker than 900 × $10^6$ spz/ml may, however, prove to be suitable.

The temperature of the semen diluted in the first step of the present process is generally lowered from 30°C in about 2 hours, as has been said hereinabove. The diluent 102 is introduced at the temperature of 4°C. Tests have shown that the incorporation of glycerol at about 30°C resulted in lower fertility of spermatozoa.

According to the present invention, glycerolization, that is to say, the addition of the diluent 102, starts about two hours after the first dilution and is preferably carried out in two steps with a 20 minute interval.

The contact time of the diluted semen and the diluent 102 is about 2 hours to 2½ hours.

Freezing of the semen diluted according to the invention is carried out by the method of freezing in straws; said method consists in conditioning the diluted semen in straws, for example of a useful volume of 0.45 ml and in freezing the said straws by immersing them horizontally in nitrogen vapor, at a height corresponding to a temperature of about −75°C. Immersion is maintained for about 8 minutes.

The quality of the frozen semen can start to be tested as from the second day after freezing, but it is desirable to wait for about two weeks. The quality of the semen is tested under the following conditions: the temperature of thawing is 35°–38°C, the semen incubation temperature is also +38°C; an aqueous solution of sodium citrate 5.5$H_2O$ (31.25g of salt in one liter of solution) is used as a redilution medium for the thawed semen. The reheated semen is diluted at a rate of 2 ml citrate solution for the content of one straw. The percentage of live spermatozoa is determined with a phase-contrast microscope 0.1 and 3 hours after redilution and also at a temperature of 38°C. Tests have shown that any ejaculate having a percentage of live spermatozoa of 45% or more immediately after redilution at 38°C, of 40% or more one hour after redilution and 30% or more three hours after redilution, can be used. The rediluted semen was maintained permanently at a temperature of 38°C. The rate of lambing observed after artificial insemination of ewes with ram semen frozen according to the invention under normal conditions are always higher than 50%, and can be as high as 70%.

Thus, the present invention provides a process which gives lambing rates higher than those obtained with the processes of the prior art.

It is another object of the present invention to provide a diluent useful in the process of the invention, that is to say, the diluent consisting of
1. a diluent without glycerol and comprising lactose and egg yolk;
2. a diluent with glycerol and comprising powdered milk and sodium citrate.

The first diluent without glycerol preferably contains 80% of a 10.3% lactose solution (weight by volume) and 20% egg yolk (in volume per volume).

The second diluent is preferably obtained, as has been indicated hereinabove, starting with the "diluent L" comprising powdered milk, by increasing the milk content of said diluent. Diluent L, which is known, contains 10 parts by weight of powdered milk, 90 parts by volume of distilled water and 0.3 parts by weight of sulfamide. At the end of the preparation, 100 UI of penicillin and 0.1 parts by weight of streptomycin are added. Said diluent L and the method for obtaining same are described in the above-mentioned article by G. Colas (1968).

The invention also relates to the ram semen diluted according to the process described above and the solution of diluted ram semen after thawing of said diluted ram semen.

The invention also makes it possible to perform artificial insemination immediately after thawing.

The invention will be illustrated in greater detail by the following examples which are in no way limiting.

EXAMPLE 1

1.5 ml of ram semen from a ram of the "Ile de France" breed was collected, the motility of the spermatozoa was 4.7 and the concentration of pure semen was $4.2 \times 10^9$ spz/ml. The so collected semen was diluted at 30°C in 2.7 ml of a diluent 101 containing 10.3% lactose and 20% egg yolk. The so obtained mixture was then cooled to 4°C in 2 hours. The above mixture was then diluted, at 4°C, in 2.8 ml of the diluent 102 containing 14.3% powdered milk, 10% glycerol and the pH of which had been adjusted to 6.6–6.65 with a 28.57% sodium citrate solution; the diluent 102 was added in two steps with an interval of 20 minutes betweem them. Two hours after the first addition of the diluent 102, the diluted semen was conditioned in straws of 0.45 ml useful volume and freezing was performed under the usual conditions in liquid nitrogen vapor at between −70° and −80°C. The quality of the frozen semen was tested 15 days after freezing. The semen was thawed at 38°C; the redilution medium was an aqueous solution of 31.25% sodium citrate 5.5 $H_2O$. Each straw was diluted in 2 ml of the above citrate solution, and the percentage of live spermatozoa was determined 0.1 and 3 hours after redilution. The obtained results are given in the following table:

| time in hours after redilution | % of live spermatozoa |
|---|---|
| 0 | 50 |
| 1 | 40 |
| 3 | 32.5 |

EXAMPLE 2

Ewes of the "Ile de France" breed were artificially inseminated in October, with semen preserved by freezing according to example 1. The ewes were treated by the hormonal method (vaginal sponge soaked with 40 mg of fluorogestone acetate —400 IU of PMSG the day the sponge is removed). Two inseminations were performed on each ewe 50 and 60 hours after removal of the sponge. A lambing rate of 60% was obtained.

EXAMPLE 3

In this example, the influence of the final concentration of glycerol in the diluted semen was studied. Two diluents 102 were prepared as in example 1, one containing 10% glycerol and the other 5% glycerol. The freshly collected ram semen was diluted under the same conditions as in example 1 with the two diluents. The contents of glycerol in the diluted semen were, therefore, 4% in one case and 2% in the other. 91 ewes of the same breeding were inseminated as in example 2 with the diluted semen containing 2% glycerol and 79 ewes of the same breeding were inseminated under the same conditions with the diluted semen containing 4% glycerol. The following lambing rates were obtained:

| Glycerol content in the diluted semen | % of lambing |
|---|---|
| 2% | 38.5% |
| 4% | 55.7% |

This test shows that is is advantageous in the process of the invention to use a glycerol content of about 4%.

EXAMPLE 4

One batch of 34 ewes of a same breeding was inseminated with ram semen diluted according to the invention prepared as in example 1 and a second batch of 45 ewes from the same breeding with ram semen diluted under the same conditions as in example 1, but instead of using the diluent 102 as the second diluent, that is to say the glycerol-containing diluent, a known diluent containing 11.75% lactose, 10% glycerol and 20% egg yolk was used. Lambing rates of 73.5% were obtained with the diluent according to the invention, whereas the lambing rate with the known diluent was only 42.2%.

This example shows that the results obtained with a second diluent which, according to the invention, is enriched with milk, are more advantageous than with a conventional diluent containing no milk.

EXAMPLE 5

In this example, the diluent according to the present invention was compared in vivo with a diluent supplied by the "International Genes" center, 1935—West County Road B-2, St. Paul, Minnesota 55–113, United States of America.

One batch of ewes was inseminated with the diluent according to the invention and another batch of the same breeding was inseminated with the above-mentioned diluent. The tests were effected during the natural oestrus and the synchronized oestrus.

The obtained results are given in the table I.

EXAMPLE 6

In this example, glycerdization, that is to say, the addition of diluent 102, to semen diluted at 30°C with diluent 101 of the invention, was effected first at 30°C, and second according to the invention, that is to say at 4°C, the other conditions for carrying out the dilution and freezing process being identical to those of example 1. 23 ewes were inseminated as in example 2 with the diluent of the invention and 23 ewes from the same breeding were inseminated with diluted semen glycerolized at 30°C. Lambing rates of 35% were obtained with the diluent glycerolized at 30°C and of 48% with the diluent glycerolized at 4°C. These results show that higher rates of pregnancies were obtained when glycerolization was effected at 4°C.

EXAMPLE 7

In this example, the test was carried out as in example 1, using ram semen, which had not been selected for motility of spermatozoa, using as second diluent, on the one hand, the "diluent L" which was not enriched with milk and, on the other hand, the diluent 102 according to the invention. The average number of live spermatozoa 0.1 and 3 hours after thawing was 19.2% in the case of diluent L and 25.9% in the case of diluent 102. This example shows that diluent 102 according to the invention is more advantageous than the non-enriched diluent L, even for freezing ejaculates which have not been selected prior to dilution.

TABLE I

|  | Natural oestrus | Synchronized oestrus | Average |
|---|---|---|---|
| Semen diluted according to prior art |  |  |  |
| Fertility (% lambing) | 59.0 (56) | 52.0 (96) | 55 (152) |
| Prolificacy (% lambs dropped) | 163 | 180 | 173 |
| Semen diluted according to the invention |  |  |  |
| Fertility | 68 (60) | 75.0 (94) | 73 (154) |
| Prolificacy | 185 | 200 | 193 |

I claim:
1. In a process for the preparation of ram semen consisting in diluting the freshly collected semen in a diluent without glycerol and then in a diluent with glycerol and in subsequent freezing of the diluted semen, the improvement comprising the steps of:
   a. diluting the freshly collected semen in a glycerol-free first diluent containing lactose and egg yolk,
   b. cooling the mixture obtained in step (a) to a temperature less than about 5°C,
   c. diluting the mixture obtained in step (b) in a second diluent containing glycerol, powdered milk and sodium citrate, the amount of glycerol being such that the final glycerol concentration of the diluted semen is at most about 4%,
   d. conditioning in straws the so diluted semen and freezing.

2. A process according to claim 1, wherein the diluent without glycerol contains preferably up to 20% egg yolk and the second diluent is a concentrated aqueous solution of powdered milk containing glycerol, the pH of which is adjusted to a value between 6 and 7 by means of sodium citrate solution.

3. The process according to claim 2, wherein the pH of the second diluent is within the range of about 6.60–6.65.

4. The process according to claim 1, wherein the first dilution is carried out at a temperature in the range of 25° to 32°C and the second dilution is carried out at a temperature in the range of 3° to 5°C.

5. The process according to claim 4, wherein the first dilution is carried out at about 30°C and the second one is carried out at about 4°C.

6. The process according to claim 4, wherein the temperature is lowered between the first and the second dilution over 2 to 3 hours.

7. The process according to claim 6, wherein the temperature is lowered over about 2 hours.

8. The process according to claim 1, wherein the second dilution is carried out in two steps with an interval of about twenty minutes between them.

9. The process according to claim 1, wherein the freezing starts about 2 to 2½ hours after the addition of the glycerol-containing diluent.

10. The process according to claim 8, wherein the freezing starts about 2 to 2½ hours after the first addition of the glycerol-containing diluent.

11. The process according to claim 1, wherein the amount of glycerol in the second diluent is such that the final glycerol concentration in the diluted semen is about 4%.

12. The process according to claim 1, wherein the freezing is carried out at a temperature of about −75°C.

13. The process according to claim 1, wherein the diluent comprising lactose and egg yolk contains 80% of a 10.3% lactose solution (by weight per volume) and 20% of an egg yolk solution (volume per volume) and in that the second diluent is obtained from "diluent L" containing 10.3% powdered milk, by adding to 100 ml of said diluent/L at least 4g of powdered milk, the pH of the solution so obtained being adjusted to 6.60–6.65 by means of a concentrated sodium citrate solution, the amount of glycerol used in said diluent being 10% by volume.

14. A solution of frozen ram semen obtained according to claim 1.

15. Ram semen in straws obtained according to claim 1.

* * * * *